(12) United States Patent
Bracken et al.

(10) Patent No.: US 12,251,486 B2
(45) Date of Patent: Mar. 18, 2025

(54) VEHICLE SANITIZING SYSTEMS AND METHODS FOR USING THE SAME

(71) Applicant: Toyota Motor North America, Inc., Plano, TX (US)

(72) Inventors: Daniel C. Bracken, Frisco, TX (US); Joshua Batie, Frisco, TX (US); Michael D. Dorazio, Santa Monica, CA (US); Randy Kaushek, Rancho Santa Margarita, CA (US); James H. Kikuma, Plano, TX (US); Judy K. Chen, Dallas, TX (US); Juan Acosta, The Colony, TX (US); Sergei I. Gage, Dallas, TX (US)

(73) Assignee: Toyota Motor North America, Inc., Plano, TX (US)

( * ) Notice: Subject to any disclaimer, the term of this patent is extended or adjusted under 35 U.S.C. 154(b) by 854 days.

(21) Appl. No.: 17/470,753

(22) Filed: Sep. 9, 2021

(65) Prior Publication Data

US 2023/0072695 A1    Mar. 9, 2023

(51) Int. Cl.
*A61L 2/24* (2006.01)
*A61L 2/20* (2006.01)

(52) U.S. Cl.
CPC .............. *A61L 2/24* (2013.01); *A61L 2/202* (2013.01); *A61L 2202/14* (2013.01); *A61L 2202/25* (2013.01)

(58) Field of Classification Search
CPC ............................. A61L 2/24; A61L 2202/14
See application file for complete search history.

(56) References Cited

U.S. PATENT DOCUMENTS

| 7,846,971 | B2 | 12/2010 | Najafi et al. | |
| 11,771,786 | B1 * | 10/2023 | Glidden | A61L 2/04 422/3 |
| 2019/0176768 | A1 | 6/2019 | Diaz Garcia et al. | |
| 2019/0351768 | A1 | 11/2019 | Salter et al. | |
| 2020/0198445 | A1 | 6/2020 | Line et al. | |
| 2021/0353785 | A1 * | 11/2021 | Bonutti | A23L 3/28 |

(Continued)

FOREIGN PATENT DOCUMENTS

| CN | 2761451 Y | 3/2006 |
| CN | 202896237 U | 4/2013 |

(Continued)

*Primary Examiner* — Donald R Spamer
*Assistant Examiner* — Kayla Rose Sarantakos
(74) *Attorney, Agent, or Firm* — Dinsmore & Shohl LLP

(57) ABSTRACT

A vehicle system includes a vehicle body defining a vehicle interior and a vehicle exterior, one or more detection devices including at least one of a microphone and a camera structurally configured to receive data indicative of conditions within the vehicle interior or on the vehicle exterior, a sanitization device, and a controller communicatively coupled to the one or more detection devices and the sanitization device, the controller including a processor and a non-transitory computer readable and executable instruction set, which when executed, causes the processor to receives data from the one or more detection devices, determine a surface at least one of within the vehicle interior or on the vehicle exterior contacted by a user based at least in part on the data from the one or more detection devices, and direct the sanitization device to sanitize the surface.

16 Claims, 4 Drawing Sheets

(56) References Cited

U.S. PATENT DOCUMENTS

| | | | | |
|---|---|---|---|---|
| 2022/0012894 A1* | 1/2022 | Lev | ............................ | G01J 5/00 |
| 2022/0188716 A1* | 6/2022 | Mathieu | .................. | G16H 50/30 |
| 2023/0126753 A1* | 4/2023 | Kikuma | .................... | A61L 2/24 |
| | | | | 422/28 |

FOREIGN PATENT DOCUMENTS

| | | | |
|---|---|---|---|
| CN | 107375976 | A | 11/2017 |
| CN | 109263439 | A | 1/2019 |
| CN | 208591353 | U | 3/2019 |
| CN | 109908388 | A | 6/2019 |
| CN | 110065475 | A | 7/2019 |
| CN | 209063855 | U | 7/2019 |
| CN | 211765160 | U | 1/2020 |
| CN | 111110890 | A | 5/2020 |
| CN | 111302190 | A | 6/2020 |
| EP | 3402686 | A1 | 11/2018 |
| JP | 2006341759 | A | 12/2006 |
| JP | 6107278 | B2 | 4/2017 |
| KR | 100178167 | B1 | 4/1999 |
| KR | 100740903 | B1 | 7/2007 |
| KR | 100836396 | B1 | 6/2008 |
| KR | 2015013729 | A | 12/2015 |
| KR | 101663216 | B1 | 10/2016 |
| KR | 101885736 | B1 | 8/2018 |
| KR | 20190002392 | A | 1/2019 |
| KR | 102000972 | B1 | 7/2019 |
| KR | 101987397 | B1 | 9/2019 |
| KR | 102087940 | B1 | 3/2020 |
| KR | 1020735610000 | B1 | 3/2020 |
| WO | 03076583 | A2 | 9/2003 |
| WO | 2019139743 | A1 | 7/2019 |
| WO | 2020110134 | A1 | 6/2020 |

\* cited by examiner

VEHICLE SANITIZING SYSTEMS AND METHODS FOR USING THE SAME

TECHNICAL FIELD

The present specification generally relates to vehicle sanitizing systems, and methods for operating the same.

BACKGROUND

Vehicles such as automobiles, buses, and the like can be utilized to transport passengers from place to place. Some vehicles may be operated by users that are different from the passengers of the vehicle. For example, buses may be operated by a driver and may carry numerous passengers. Similarly, taxis, rideshares, and the like may be operated by a driver and may carry numerous passengers. In many vehicles, the driver and passengers are generally positioned within an interior of the vehicle.

SUMMARY

Various contagions, such as viruses and the like may be transmitted through the air and/or through contact surfaces (e.g., surfaces contacted by a person carrying the contagion). In some instances, contagions can be more readily transmitted between individuals within an interior of a vehicle, as compared to individuals spaced apart from one another in open-air environments. Additionally, contagions can be deposited on various surfaces of the vehicle as different passengers contact the various surfaces, and the contagions can subsequently transmitted to other passengers and/or the driver of the vehicle. Further, in some circumstances, the vehicle and driver may be exposed to numerous passengers, for example where the vehicle is used in public transit or is a vehicle for hire. As the number of passengers the driver and the vehicle are exposed to increases, the likelihood of coming into contact with an infected passenger increases.

To reduce the transmission of contagion between persons, it is desirable to sanitize vehicle surfaces contacted by the vehicle passengers. Embodiments of the present application are generally directed to systems and methods for detecting surfaces contacted by vehicle passengers, and directing a sanitization device to sanitize the surfaces contacted by the vehicle passengers. In some embodiments, the sanitization of the surfaces contacted by the vehicle passengers is tailored to the type of contact (e.g., direct contact, contact with the passenger's saliva, etc.). In some embodiments, the vehicle can be routed to a medical facility in response to detecting certain types of contact, such as vomit or the like.

In one embodiment, a vehicle system includes a vehicle body defining a vehicle interior and a vehicle exterior, one or more detection devices including at least one of a microphone and a camera structurally configured to receive data indicative of conditions within the vehicle interior or on the vehicle exterior, a sanitization device, and a controller communicatively coupled to the one or more detection devices and the sanitization device, the controller including a processor and a non-transitory computer readable and executable instruction set, which when executed, causes the processor to receives data from the one or more detection devices, determine a surface at least one of within the vehicle interior or on the vehicle exterior contacted by a user based at least in part on the data from the one or more detection devices, and direct the sanitization device to sanitize the surface.

In another embodiment, a method for sanitizing a vehicle includes capturing at least one of an image or a sound from at least one of a vehicle interior or a vehicle exterior with one or more detection devices, determining a surface at least one of within the vehicle interior or on the vehicle exterior contacted by a user based at least in part on the at least one of the image or the sound from the one or more detection devices, and sanitizing the surface automatically with a sanitization device.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Embodiments of the present application are generally directed to systems and methods for detecting surfaces contacted by vehicle passengers, and directing a sanitization device to sanitize the surfaces contacted by the vehicle passengers. In some embodiments, the sanitization of the surfaces contacted by the vehicle passengers is tailored to the type of contact (e.g., direct contact, contact with the passenger's saliva, etc.). In some embodiments, the vehicle can be routed to a medical facility in response to detecting certain types of contact, such as vomit or the like. These and other embodiments will now be described with reference to the figures.

Figure 1:
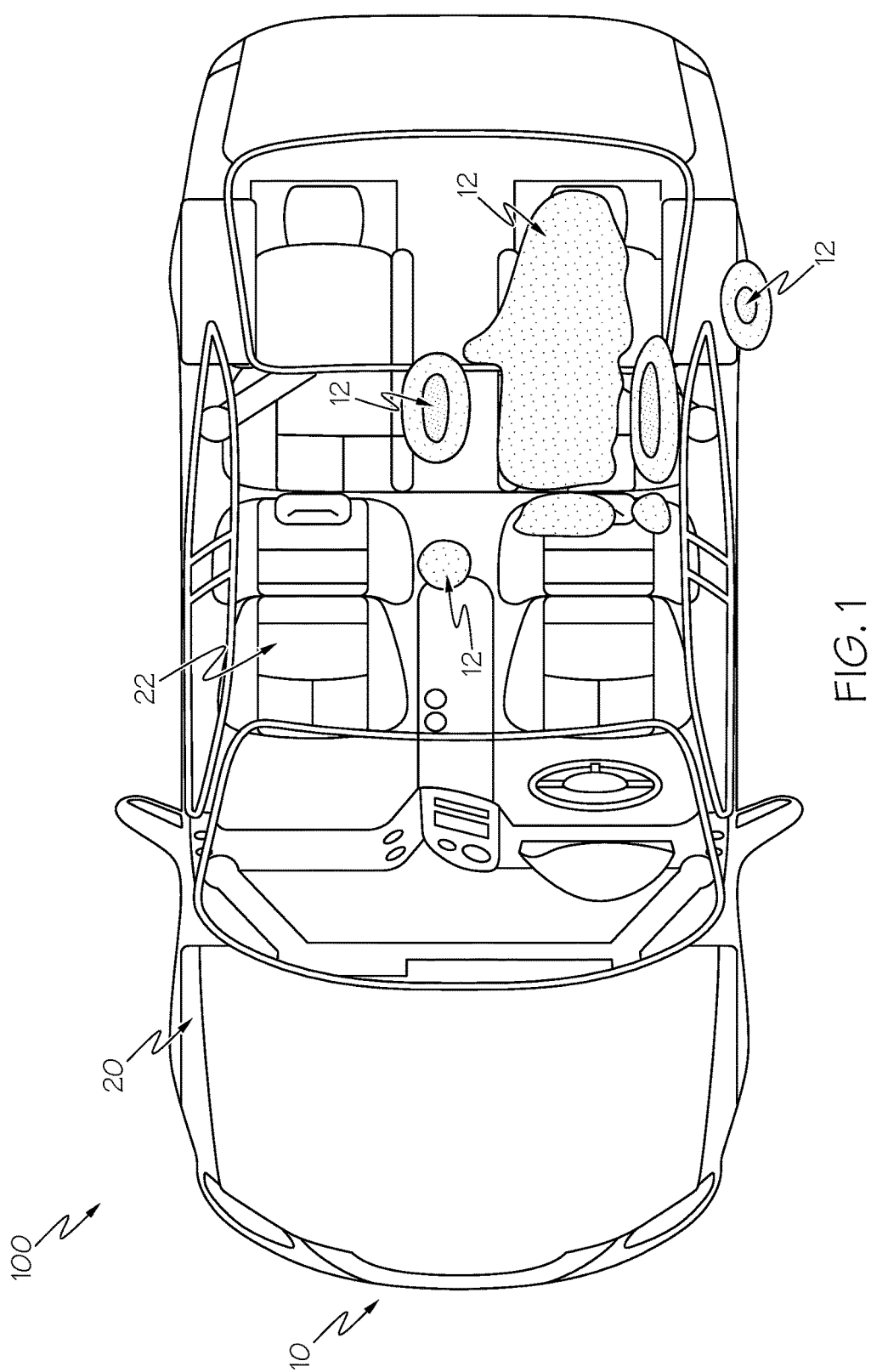
FIG. 1 schematically depicts a vehicle and a vehicle system, according to one or more embodiments shown and described herein.

Referring initially to FIG. 1, a vehicle 10 including a vehicle system 100 is schematically depicted. In embodiments, the vehicle 10 includes a vehicle body defining a vehicle exterior 20 and a vehicle interior 22. The vehicle 10 defines one or more surfaces 12 on the vehicle exterior 20 and the vehicle interior 22. The one or more surfaces 12 generally include surfaces that a user, such as a passenger may contact. For example, the one or more surfaces 12 can include the seats of the vehicle 10, door handles, window controls, console surfaces, seat backs and the like. In embodiments, the one or more surfaces 12 may be contacted by the passengers directly (e.g., via touch and the like), may be contacted by fluids from the passenger (e.g., via saliva droplets, sweat, vomit, or the like), or may be contacted by objects on the passenger's person (e.g., a cellphone, tablet, and/or the like).

Figure 2:
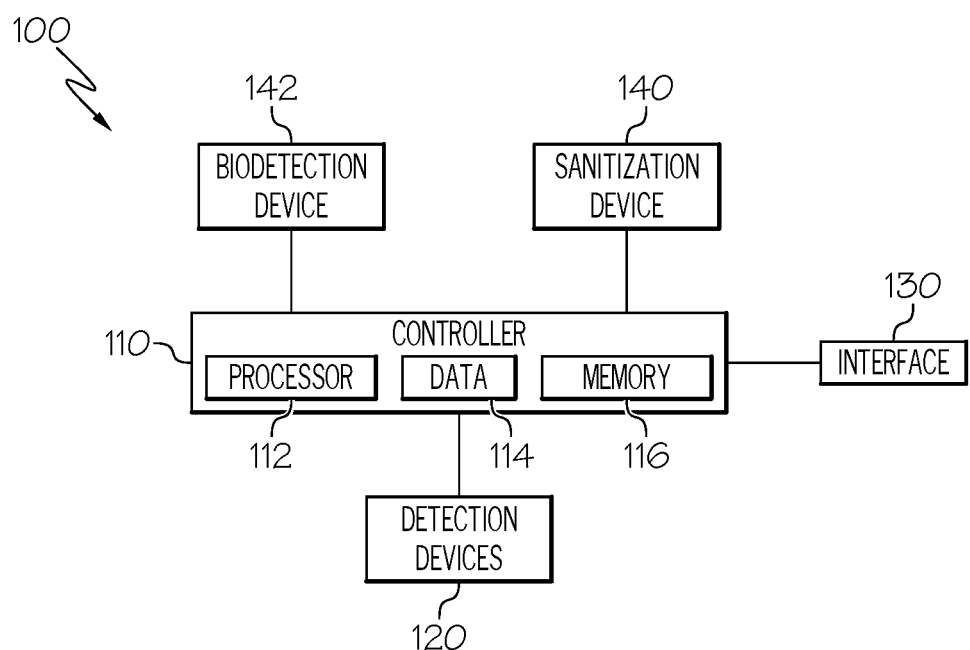
FIG. 2 schematically depicts a control diagram of the vehicle system of FIG. 1, according to one or more embodiments shown and described herein.

Referring to FIG. 2, a control diagram of the vehicle system 100 is schematically depicted. In embodiments, the vehicle system 100 includes a controller 110. In some embodiments, the controller 110 includes a processor 112, a data storage component 114, and/or a memory component 116. The memory component 116 may be configured as volatile and/or nonvolatile memory and as such, may include random access memory (including SRAM, DRAM, and/or other types of RAM), flash memory, secure digital (SD) memory, registers, compact discs (CD), Bernoulli cartridges, digital versatile discs (DVD), and/or other types of non-transitory computer-readable mediums. Depending on the particular embodiment, these non-transitory computer-readable mediums may reside within the controller 110 and/or external to the controller 110.

The memory component 116 may store operating logic, analysis logic, and communication logic in the form of one or more computer readable and executable instruction sets. The analysis logic and the communication logic may each include a plurality of different pieces of logic, each of which may be embodied as a computer program, firmware, and/or hardware, as an example. A local interface is also included in the controller 110, and may be implemented as a bus or other communication interface to facilitate communication among the components of the controller 110.

The processor 112 may include any processing component operable to receive and execute instructions (such as from a data storage component 114 and/or the memory component 116). It should be understood that while the components in FIG. 2 are illustrated as residing within the controller 110, this is merely an example, and in some embodiments, one or more of the components may reside external to the controller 110. It should also be understood that, while the controller 110 is illustrated as a single device, this is also merely an example.

In embodiments, the controller 110 is communicatively coupled to one or more components of the vehicle system 100. For example, in the embodiment depicted in FIG. 2, the controller 110 is communicatively coupled to one or more detection devices 120, an interface 130, one or more sanitization devices 140, and one or more biodetection devices 142.

Referring to FIGS. 1 and 2, the one or more detection devices 120 are structurally configured to detect conditions within the vehicle interior 22 and/or on the vehicle exterior 20. In some embodiments, the one or more detection devices 120 include, for example and without limitation, audio microphones, video and/or photographic cameras, thermal imaging cameras, and/or the like. The one or more detection devices 120 are structurally configured to detect conditions within the vehicle interior 22 and/or on the vehicle exterior 20 by capturing sounds and/or images within the vehicle interior 22 and/or on the vehicle exterior 20, as described in greater detail herein. In embodiments, the one or more detection devices 120 are communicatively coupled to the controller 110 such that the one or more detection devices 120 can send signals to and/or receive signals from the controller 110.

In some embodiments, the vehicle system 100 further includes the interface 130 communicatively coupled to the controller 110. The interface 130 is communicatively coupled to the controller 110 such that the interface 130 can send signals to and/or receive signals from the controller 110. The interface 130 may display information related to the operation of the vehicle system 100, and may include for example and without limitation, a graphical user interface (GUI), or the like. In some embodiments, the interface 130 may be positioned within an interior of the vehicle 10, for example on an instrument panel or other suitable location within the vehicle 10. In some embodiments, the interface 130 may be positioned external to the vehicle 10. While reference is made herein to a single interface 130, it should be understood that this is merely an example, and in embodiments described herein, multiple interfaces 130 may be communicatively coupled to the controller 110.

In some embodiments, the vehicle system 100 includes the one or more biodetection devices 142 communicatively coupled to the controller 110. For example, the one or more biodetection devices 142, in embodiments, can send signals to and/or receive signals from the controller 110. The one or more biodetection devices 142 may be structurally configured to detect airborne pathogens. For example the one or more biodetection devices 142 can detect the presence of viruses, bacteria, and/or the like in air within the vehicle interior 22 and/or around the vehicle exterior 20.

The sanitization device 140 is communicatively coupled to the controller 110 such that the sanitization device 140 can receive signals from and/or send signals to the controller 110. In embodiments, the sanitization device 140 may include any suitable device for sanitizing the vehicle interior 22 and/or the vehicle exterior 20. For example the sanitization device 140 may include a device that dispenses sanitizing gas and/or fluid, for example and without limitation, ozone, alcohol, bleach, and/or the like. The controller 110 can direct the sanitization device 140 to sanitize the surfaces 12 (FIG. 1) of the vehicle 10 (FIG. 1), as described in greater detail herein.

Figure 3:
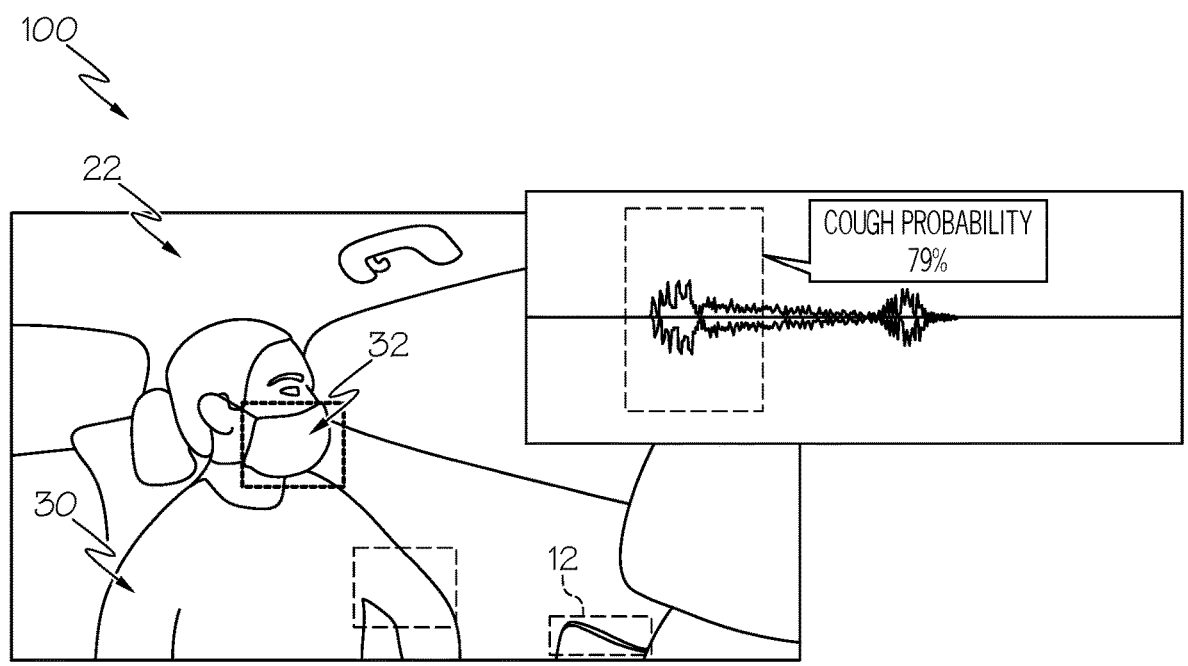
FIG. 3 schematically depicts a passenger within the vehicle of FIG. 1, according to one or more embodiments shown and described herein.
Figure 4:
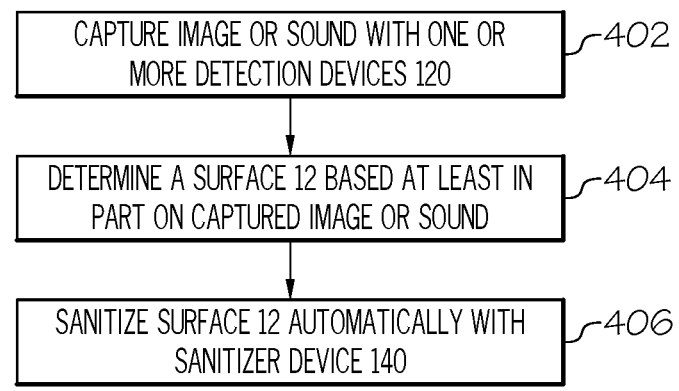
FIG. 4 is a flowchart of another method for operating the vehicle of FIG. 1, according to one or more embodiments shown and described herein.

Referring to FIGS. 2 and 3, a user 30 is depicted within the vehicle interior 22. In embodiments, the one or more detection devices 120 and/or the one or more biodetection devices 142 determine one or more surfaces 12 contacted by the user 30. In the embodiment depicted in FIGS. 2 and 3, the one or more detection devices 120 include a microphone or the like that captures sounds within the vehicle interior 22. The microphone of the one or more detection devices 120 may be configured to capture sounds within the vehicle interior 22, and the controller 110 may be configured to receive signals from the from the one or more detection devices 120 indicative of the sound detected within the vehicle interior 22. In some embodiments, the controller 110 analyzes the signals received from the one or more detection devices 120 to determine the nature of the sounds detected by the one or more detection devices 120. In some embodiments, the controller 110 determines whether the sounds detected by the one or more detection devices 120 are associated with likely emission of bodily fluids (e.g., coughing, sneezing, talking, or the like). In the example of FIGS. 2 and 3, the controller 110 is shown as analyzing a sound from the vehicle interior 22, and determines a likelihood that the detected sound is indicative of a user 30 coughing (e.g., at a 79% probability that the detected sound is of a user 30 coughing within the vehicle interior 22). Based at least in part on the detected sound from the vehicle interior 22, the controller 110 determines a surface 12 contacted by the user 30. In the example of the user 30 coughing, the controller 110 may determine that surfaces 12 positioned forward of the user 30 have been contacted by the user 30 (e.g., via saliva droplets emitted by the user 30).

As shown in FIGS. 2 and 3, the one or more detection devices 120 may include a camera or the like that captures images of the vehicle interior 22 and/or the vehicle exterior 20 (FIG. 1). The one or more detection devices 120 may send signals to the controller 110 indicative of captured images of the vehicle interior 22 and/or the vehicle exterior

20 (FIG. 1). The controller 110 may be configured to analyze the captured images, and may include image recognition software and the like. In embodiments, the controller 110, via the captured images, can determine surfaces 12 contacted by the user 30. The controller 110 may determine that the user 30 has contacted the door handle with the user 30's hand when entering or exiting the vehicle 10 (FIG. 1). As another example, the controller 110 may determine surfaces 12 contacted by the user 30 utilizing both sounds and images from the one or more detection devices 120. In some embodiments, the controller 110 analyzes sounds detected by the one or more detection devices 120 to determine that a user 30 has contacted one or more surfaces 12 (e.g., via coughing, sneezing, talking, or the like). The controller 110 may additionally analyze images from the one or more detection devices 120 to determine which surfaces 12 may have been contacted by the user 30, for example, via determining which direction the user 30's nose and mouth were facing when the sounds (e.g., the coughing, sneezing, talking, or the like) were detected.

In some embodiments, the controller 110 determines whether the user 30 is wearing protective equipment, shown in FIG. 3 as a mask 32 covering the user 30's nose and mouth. By determining whether the user 30 is wearing protective equipment (e.g., the mask 32), the controller 110 may determine which surfaces 12 may likely have been contacted by the user 30. For example and without being bound by theory, protective equipment such a mask 32 covering the user 30's nose and mouth can be effective at restricting the transmission of saliva droplets from the user 30. Accordingly, surfaces 12 contacted by a user 30 sneezing, coughing, talking, or the like without the mask 32 may not necessarily be contacted by a similarly situated user 30 sneezing, coughing, talking, or the like while wearing the mask 32. In this way, by determining whether the user 30 is wearing protective equipment (e.g., the mask 32), the controller 110 can more accurately determine which surfaces 12 have been contacted by the user 30.

Subsequent to determining the surfaces 12 contacted by the user 30, the controller 110 directs the sanitization device 140 to sanitize the surfaces 12 contacted by the user 30. For example, at the end of a ride (in the instance in which the vehicle 10 (FIG. 1) is used in as a rideshare, taxi, or the like), the controller 110 directs the sanitization device 140 to sanitize the surfaces 12 contacted by the user 30.

Referring to FIGS. 1 and 2, the controller 110 may generate a "heat map" of surfaces 12 contaminated by the user 30 (FIG. 3). In some embodiments, the controller 110 determines one or more contaminated surfaces of the plurality of surfaces 12 based at least in part on data from the one or more detection devices 120, the one or more contaminated surfaces exceeding a configurable contamination threshold. In embodiments, the configurable contamination threshold can be a threshold associated with the likelihood that the user 30 (FIG. 3) has contacted the surface 12. The controller 110 generates a "heat map" as shown in FIG. 1, indicating the one or more contaminated surfaces within the vehicle interior 22 or on the vehicle exterior 20. In some embodiments, the controller 110 directs the sanitization device 140 to sanitize the one or more contaminated surfaces 12 according to the heat map shown in FIG. 1.

Referring to FIGS. 1-4, an example flowchart of a method of operating the vehicle system 100 is schematically depicted. At block 402, data (e.g., images and/or sounds) is captured with the one or more detection devices 120. At block 404, a surface 12 at least one of within the vehicle interior 22 or on the vehicle exterior 20 contacted by the user 30 is determined (for example by the controller 110) based at least in part on the data (e.g., images and/or sounds) from the one or more detection devices 120. In some embodiments, the controller 110 determines a type of contact based at least in part on the data from the one or more detection devices 120. In some embodiments, the controller 110 determines whether the surface 12 was contacted directly by the user 30 (e.g., via touch or the like), was contacted by fluids from the user 30 (e.g., via saliva droplets, sweat, vomit, or the like), or was contacted by objects on the user 30's person (e.g., a cellphone, tablet, and/or the like). At block 406, the controller 110 directs the sanitization device 140 to sanitize the surface 12.

In embodiments, the sanitization of the surface 12 with the sanitization device 140 is based at least in part the type of contact determined by the controller 110. As one example, in response to determining that the surface 12 was contacted directly by the user 30 via touch or was contacted by objects on the user 30's person, the sanitization device 140 is directed to sanitize the surface 12 with sanitizing fluid and/or a sanitizing wipe, such as alcohol or an alcohol wipe or the like. By contrast, in response to determining that the surface 12 was contacted by the user 30 vial fluids from the user 30 (e.g., via saliva droplets, sweat, vomit, or the like), the sanitization device 140 is directed to apply additional sanitization to the surface 12. In some embodiments, in response to determining that the surface 12 was contacted by the user 30 via fluids from the user 30 the controller 110 directs the sanitization device 140 to sanitize the surface 12 with a sanitizing gas, such as ozone or the like. In response to determining that the surface 12 was contacted by the user 30 via fluids from the user 30, the controller 110 directs the sanitization device 140 to additional sanitize the surface 12 with sanitizing fluid and/or a sanitizing wipe such as alcohol and/or an alcohol wipe. In this way, the type of sanitization administered by the sanitization device 140 can be tailored to the type of touch detected.

In some embodiments, the controller 110 receives an image of the user 30 at least one of within the vehicle interior 22 or outside the vehicle exterior 20 and determines whether the user 30 is wearing protective equipment, such as the mask 32. In some embodiments, the controller 110 directs the sanitization device 140 to sanitize the surface 12 based at least in part in response to determining whether the user 30 is wearing protective equipment. In response to determining that the user 30 is not wearing protective equipment (e.g., the mask 32), the controller 110 directs the sanitization device 140 to sanitize the surface 12 with a sanitizing gas such as ozone or the like, and/or sanitize the surface 12 with sanitizing fluid and/or a sanitizing wipe. By contrast, in response to determining that the user 30 is wearing protective equipment (e.g., the mask 32), the controller 110 may, in some embodiments, not direct the sanitization device 140 to sanitize the surface 12. In response to determining that the user 30 is wearing protective equipment (e.g., the mask 32), some embodiments of the controller 110 may direct the sanitization device 140 to sanitize the surface 12 with a different type of sanitization as compared to in response to determining that the user 30 is not wearing protective equipment. In some embodiments, the controller 110 directs the sanitization device 140 to sanitize the surface 12 with a sanitizing fluid and/or a sanitizing wipe in response to determining that the user 30 is wearing protective equipment (e.g., the mask 32). By contrast, in some embodiments, the controller 110 directs the sanitization device 140 to sanitize the surface 12 with the sanitizing fluid and/or the sanitizing wipe, and additionally with a sanitizing gas, such as ozone or the like.

Based at least in part in response to receiving data from the one or more detection devices 120 indicative of certain types of contact, the controller 110 causes the interface 130 to present an alert. In response to receiving data from the one or more detection devices 120 indicative of the user 30 vomiting, coughing severely (e.g., coughing with an intensity and/or duration exceeding a predetermined threshold), the controller 110 directs the interface 130 to present an alert. In embodiments, the alert may be a visual or audible alert visible/audible to the driver or operator of the vehicle 10. By providing the alert via the interface 130, the driver or operator of the vehicle 10 can be alerted to certain types of contact that may require immediate attention.

Based at least in part on data from the one or more detection devices 120, the controller 110 changes a planned navigation route. In response to receiving data from the one or more detection devices 120 data from the one or more detection devices 120 indicative of the user 30 vomiting, coughing severely (e.g., coughing with an intensity and/or duration exceeding a predetermined threshold), the controller 110 directs the interface 130 to display a navigation route to a nearby medical facility. In some embodiments, for example in embodiments in which the vehicle 10 is autonomous or semi-autonomous, in response to receiving data from the one or more detection devices 120 indicative of the user 30 vomiting, coughing severely (e.g., coughing with an intensity and/or duration exceeding a predetermined threshold), the controller 110 directs the vehicle 10 to drive toward the nearby medical facility. In this way, the vehicle system 100 may assist in obtaining assistance to the user 30 in certain situations.

In some embodiments, the controller 110 the type of sanitization the controller 110 directs the sanitization device 140 to sanitize the surface 12 based at least in part on data received from the one or more biodetection devices 142. In some embodiments, the controller 110 directs the sanitization device 140 to sanitize the surface 12 in response to receiving a signal from the one or more biodetection devices 142 indicating the presence of an airborne pathogen within the vehicle interior 22. In some embodiments, the controller 110 changes a planned navigation route based at least in part on data from the one or more biodetection devices 142. For example, in some embodiments, the controller 110 changes the planned navigation route as outlined above in response to receiving a signal from the biodetection device indicative of the presence of an airborne pathogen within the vehicle interior 22.

Accordingly, it should be understood that embodiments described herein are generally directed to systems and methods for detecting surfaces contacted by vehicle passengers, and directing a sanitization device to sanitize the surfaces contacted by the vehicle passengers. In some embodiments, the sanitization of the surfaces contacted by the vehicle passengers is tailored to the type of contact (e.g., direct contact, contact with the passenger's saliva, etc.). In some embodiments, the vehicle can be routed to a medical facility in response to detecting certain types of contact, such as vomit or the like.

Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Rather, the appended claims should be taken as the sole representation of the breadth of the present disclosure and the corresponding scope of the various embodiments described in this disclosure. Further, it should be apparent to those skilled in the art that various modifications and variations can be made to the described embodiments without departing from the spirit and scope of the claimed subject matter. Thus it is intended that the specification cover the modifications and variations of the various described embodiments provided such modification and variations come within the scope of the appended claims and their equivalents.

It is noted that recitations herein of a component of the present disclosure being "structurally configured" in a particular way, to embody a particular property, or to function in a particular manner, are structural recitations, as opposed to recitations of intended use. More specifically, the references herein to the manner in which a component is "structurally configured" denotes an existing physical condition of the component and, as such, is to be taken as a definite recitation of the structural characteristics of the component.

It is noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

For the purposes of describing and defining the present invention it is noted that the terms "substantially" and "about" are utilized herein to represent the inherent degree of uncertainty that may be attributed to any quantitative comparison, value, measurement, or other representation. The terms "substantially" and "about" are also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A vehicle system comprising:

a vehicle body defining a vehicle interior and a vehicle exterior;
one or more detection devices comprising at least one of a microphone and a camera structurally configured to receive data indicative of conditions within the vehicle interior or on the vehicle exterior;
a sanitization device; and
a controller communicatively coupled to the one or more detection devices and the sanitization device, the controller comprising a processor and a non-transitory computer readable and executable instruction set, which when executed, causes the processor to:
receive data from the one or more detection devices;
determine a surface at least one of within the vehicle interior or on the vehicle exterior contacted by a user based at least in part on the data from the one or more detection devices;
detect a type of contact based at least in part on the data from the one or more detection devices;
direct the sanitization device to administer a first type of sanitization by the sanitization device in response to determining a first type of contact is detected by the one or more detection devices; and
direct the sanitization device to administer a second type of sanitization by the sanitization device in response to determining a second type of contact is detected by the one or more detection devices.

2. The vehicle system of claim 1, wherein the non-transitory computer readable and executable instruction set, when executed, further causes the processor to:
receive an image of the user at least one of within the vehicle interior or outside the vehicle exterior; and
determine whether the user is wearing protective equipment.

3. The vehicle system of claim 2, wherein directing the sanitization device to sanitize the surface is based at least in part in response to determining whether the user is wearing protective equipment.

4. The vehicle system of claim 1, further comprising a display communicatively coupled to the controller, wherein the non-transitory computer readable and executable instruction set, when executed, further causes the processor to direct the display to present an alert based at least in part on the data from the one or more detection devices.

5. The vehicle system of claim 1, wherein the non-transitory computer readable and executable instruction set, when executed, further causes the processor to change a planned navigation route based at least in part on the data from the one or more detection devices.

6. The vehicle system of claim 1, further comprising a biodetection device communicatively coupled to the controller, the biodetection device structurally configured to detect airborne pathogens.

7. The vehicle system of claim 1, wherein the non-transitory computer readable and executable instruction set, when executed, further causes the processor to:
determine a plurality of surfaces within the vehicle contacted by the user based at least in part on the data received from the one or more detection devices;
determine one or more contaminated surfaces of the plurality of surfaces, the one or more contaminated surfaces exceeding a configurable contamination threshold;
generate a heat map of the one or more contaminated surfaces at least one of within the vehicle interior or on the vehicle exterior; and
direct the sanitization device to sanitize the one or more contaminated surfaces according to the heat map.

8. The vehicle system of claim 1, wherein:
the non-transitory computer readable and executable instruction set, when executed, further causes the processor to determine a type of contact based at least in part on the data from the one or more detection devices;
directing the sanitization device to sanitize the surface is based at least in part on a determined type of contact; and
the non-transitory computer readable and executable instruction set, when executed, further causes the processor to:
receive an image of the user at least one of within the vehicle interior or on the vehicle exterior; and
determine whether the user is wearing protective equipment; and
direct the sanitization device to sanitize the surface is based at least in response to determining whether the user is wearing protective equipment.

9. A method for sanitizing a vehicle, the method comprising:
capturing at least one of an image or a sound from at least one of a vehicle interior or a vehicle exterior with one or more detection devices;
determining a surface at least one of within the vehicle interior or on the vehicle exterior contacted by a user based at least in part on the at least one of the image or the sound from the one or more detection devices;
detecting a type of contact based at least in part on the data from the one or more detection devices;
administering a first type of sanitization by a sanitization device in response to determining a first type of contact is detected by the one or more detection devices; and
administering a second type of sanitization by the sanitization device in response to determining a second type of contact is detected by the one or more detection devices.

10. The method of claim 9, further comprising determining whether the user is wearing protective equipment.

11. The method of claim 10, wherein sanitizing the surface automatically with the sanitization device is based at least in response to determining whether the user is wearing protective equipment.

12. The method of claim 9, further comprising displaying an alert based at least in part on the at least one of the image or the sound from at least one of the vehicle interior or the vehicle exterior.

13. The method of claim 9, further comprising changing a planned navigation route based at least in part on the at least one of the image or the sound from at least one of the vehicle interior or the vehicle exterior.

14. The method of claim 9, further comprising detecting an airborne pathogen with a biodetection device.

15. The method of claim 14, wherein sanitizing the surface with the sanitization device in response to detecting the airborne pathogen with the biodetection device.

16. The method of claim 14, further comprising changing a planned navigation route based at least in part in response to detecting the airborne pathogen with the biodetection device.

* * * * *

UNITED STATES PATENT AND TRADEMARK OFFICE
CERTIFICATE OF CORRECTION

PATENT NO. : 12,251,486 B2
APPLICATION NO. : 17/470753
DATED : March 18, 2025
INVENTOR(S) : Daniel C. Bracken et al.

Page 1 of 1

It is certified that error appears in the above-identified patent and that said Letters Patent is hereby corrected as shown below:

On the Title Page

Column 2, item (57), abstract, Line(s) 11, delete "receives" and insert --receive--, therefor.

In the Specification

In Column 1, Line(s) 33, after "subsequently", insert --be--.

In Column 1, Line(s) 62, delete "receives" and insert --receive--, therefor.

In Column 4, Line(s) 41, delete "from the from the" and insert --from the--, therefor.

Signed and Sealed this
Twenty-ninth Day of April, 2025

Coke Morgan Stewart
*Acting Director of the United States Patent and Trademark Office*